United States Patent [19]

Aufdembrink et al.

[11] Patent Number: 5,321,190
[45] Date of Patent: Jun. 14, 1994

[54] OLIGOMERIZATION OF ETHYLENE WITH A SUPPORTED NICKEL CATALYST

[75] Inventors: Brent A. Aufdembrink, Wilmington, Del.; Margaret M. Wu, Skillman, N.J.

[73] Assignee: Mobil Oil Corp., Fairfax, Va.

[21] Appl. No.: 131,360

[22] Filed: Oct. 4, 1993

Related U.S. Application Data

[62] Division of Ser. No. 992,349, Dec. 17, 1992.

[51] Int. Cl.$^5$ .................................. C07C 2/02
[52] U.S. Cl. .............................. 585/531; 585/500; 585/502; 585/510; 585/520; 585/530
[58] Field of Search ............... 585/500, 502, 510, 520, 585/530, 531

[56] References Cited

U.S. PATENT DOCUMENTS

| | | | |
|---|---|---|---|
| 3,527,839 | 9/1970 | Glockner. | |
| 4,827,064 | 5/1989 | Wu | 585/10 |
| 4,827,073 | 5/1989 | Wu | 585/530 |
| 4,831,005 | 5/1989 | Aufdembrink | 502/242 |
| 4,831,006 | 5/1989 | Aufdembrink | 502/242 |
| 4,859,648 | 8/1989 | Landis et al. | 502/242 |
| 4,902,392 | 2/1990 | Aufdembrink et al. | 208/110 |
| 4,912,277 | 3/1990 | Aufdembrink et al. | 585/455 |
| 4,929,587 | 5/1990 | Aufdembrink et al. | 502/242 |
| 4,933,310 | 6/1990 | Aufdembrink et al. | 502/71 |
| 4,935,573 | 6/1990 | Aufdembrink et al. | 585/417 |
| 4,942,021 | 7/1990 | Garwood et al. | 422/194 |
| 5,043,499 | 8/1991 | Harandi et al. | 585/301 |
| 5,105,042 | 4/1992 | Aufdembrink et al. | 585/458 |
| 5,105,051 | 4/1992 | Pelrine et al. | 585/528 |
| 5,128,303 | 7/1992 | Aufdembrink | 502/242 |
| 5,134,243 | 7/1992 | Bhore et al. | 585/533 |
| 5,155,076 | 10/1992 | Moini | 502/63 |

*Primary Examiner*—Patrick P. Garvin
*Assistant Examiner*—E. D. Irzinski
*Attorney, Agent, or Firm*—Alexander J. McKillop; Dennis P. Santini; Edward F. Kenehan, Jr.

[57] ABSTRACT

There is provided a catalyst comprising nickel supported on a pillared (e.g., silica pillared) vacancy titanate material. There is also provided a method for preparing this catalyst. This method may involve impregnating a pillared vacancy titanate material with a nickel nitrate solution. There is further provided a process for oligomerizing ethylene using this catalyst.

6 Claims, No Drawings

OLIGOMERIZATION OF ETHYLENE WITH A SUPPORTED NICKEL CATALYST

CROSS REFERENCE TO RELATED APPLICATION

This application is a division of copending U.S. application Ser. No. 07/992,349, filed Dec. 17, 1992.

BACKGROUND

There is provided a catalyst comprising nickel supported on a pillared vacancy titanate material There is also provided a method for preparing this catalyst. There is further provided a process for oligomerizing ethylene using this catalyst.

A variety of oligomerization catalysts have been utilized to convert, i.e., oligomerize, ethylene into olefinic products of higher molecular weight, e.g., to dimer, trimer, tetramer or the like. However, the character and relative proportions of the product mixture are greatly dependent upon the particular catalyst employed. One process is that of Bailey et al., U.S. Pat. No. 2,581,228, which employs a supported nickel oxide catalyst. This catalyst composition produces a product mixture consisting of dimeric products as well as olefinic products in the higher molecular weight range, e.g., trimer and tetramer products.

The oligomerization of ethylene over a supported nickel oxide catalyst is also described in U.S. Pat. No. 3,527,839, the entire disclosure of which is expressly incorporated herein by reference.

SUMMARY

There is provided a catalyst comprising nickel supported on a pillared layered vacancy titanate material, wherein each layer of said layered vacancy titanate material has the formula $$[\square_y Ti_{2-y}O_4]^{q-}$$

where $\square$ represents a vacancy site, $0<y<2$ and $q=4y$.

There is also provided a method for preparing a catalyst comprising nickel supported on a pillared layered vacancy titanate material, wherein each layer of said layered vacancy titanate material has the formula $$[\square_y Ti_{2-y}O_4]^{q-}$$

where $\square$ represents a vacancy site, $0<y<2$ and $q=4y$, said method comprising the steps of:

(a) contacting a pillared layered vacancy titanate material with a solution of a nickel compound under conditions sufficient to sorb at least a portion of said nickel compound into porous regions of the pillared layered vacancy titanate material;

(b) drying the contacted material of step (a) under conditions sufficient to leave a residue of said nickel compound in porous regions of the pillared layered vacancy titanate material; and (c) calcining the dried material of step (b) under conditions sufficient to convert said residue into nickel oxide.

There is also provided a process for oligomerizing ethylene said process comprising contacting ethylene with a catalyst under sufficient oligomerization conditions, wherein said catalyst comprises nickel supported on a pillared layered vacancy titanate material, wherein each layer of said layered vacancy titanate material has the formula $$[\square_y Ti_{2-y}O_4]^{q-}$$

where $\square$ represents a vacancy site, $0<y<2$ and $q=4y$.

DESCRIPTION

A catalyst of nickel supported on a pillared vacancy titanate material (VTM) can oligomerize ethylene to give liquid product efficiently. The liquid product can be used as starting material for chemical synthesis, gasoline or distillate fuel. The new catalyst is much more active than other supported Ni catalysts and produces liquid of higher molecular weight.

The catalyst has unexpected high activity for ethylene oligomerization, and the liquid product has high molecular weight. This high activity catalyst may be used to convert ethylene of low concentration and low value in FCC off-gas into valuable liquid products.

In general, the oligomers produced may have from 4 to 20 carbon atoms.

The oligomerization reaction may be conducted at reaction temperatures varying from about 50° C. to about 250° C., but preferably from about 100° C. to about 200° C. The reaction may be conducted at or above atmospheric pressure. Typical pressures vary from about 1 atmosphere to about 80 atmospheres with the range from about 2 atmospheres to about 35 atmospheres being preferred.

Pillared layered materials which can be used as catalyst supports in the present process are described in U.S. Pat. No. 5,128,303, the entire disclosure of which is expressly incorporated herein by reference.

The layered materials described in U.S. Pat. No. 5,128,303 comprise a layered metal oxide, wherein each layer of the metal oxide has the general formula $$[M_x\square_y Z_{2-(x+y)}O_4]^{q-}$$

wherein M is at least one metal of valence n wherein n is an integer between 0 and 7 and preferably is 2 or 3, $\square$ represents a vacancy site, Z is a tetravalent metal, preferably titanium, and wherein $$q=4y-x(n-4) \text{ and preferably is } 0.6-0.9, \ 0<x+y<2$$

The layered materials, which are used to prepare catalyst supports in accordance with the present disclosure, correspond the materials of the above formula, wherein x is zero and Z is Ti. Such materials are referred to herein as vacancy titanates.

It is to be appreciated that the term "layered" metal oxide is used herein in its commonly accepted sense to refer to a material which comprises a plurality of separate metal oxide layers which are capable of being physically displaced away from one another such that the spacing between adjacent layers is increased. Such displacement can be measured by X-ray diffraction techniques and/or by density measurements.

The present layered material may be made from a vacancy titanate starting material which contains anionic sites having interspathic cations associated therewith. Such interspathic cations may include hydrogen ion, hydronium ion and alkali metal cation.

More specifically, the present invention employs a layered metal oxide starting material in which each layer has the general formula

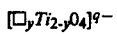

where □ represents a vacancy site, $0<y<2$ and $q=4y$.

Interposed between the layers of the oxide will be charge-balancing cations A of charge m wherein m is an integer between 1 and 3, preferably 1. Preferably A is a large alkali metal cation selected from the group consisting of Cs, Rb and K. Structurally, these metal oxides consist of layers of $(\square_y Ti_{1-y})O_6$ octahedra which are trans edge-shared in one dimension and cis edge-shared in the second dimension forming double octahedral layers which are separated by the A cations in the third dimension. These materials can be prepared by high temperature fusion of a mixture of 1) alkali metal carbonate or nitrate and 2) titanium dioxide. Such fusion can be carried out in air in ceramic crucibles at temperatures ranging between 600 to 1100° C. after the reagents have been ground to an homogeneous mixture. The resulting product is ground to 20 to 250 mesh, preferably about 100 mesh, prior to the organic swelling and intercalcation steps.

Further description of various titanometallate-type layered materials and their methods of preparation can be found in the following references:

Reid, A. F., W. G. Mumme, and A. D. Wadsley, *Acta Cryst.* B24, 1228 (1968); Groult, D., C. Mercy, and B. J. Raveau, *J. Solid State Chem.* 32, 289 (1980); England, W. A., J. E. Burkett, J. B. Goodenough, and P. J. Wiseman, *J. Solid State Chem.* 49, 300 (1983). The infinite trans-edge shared layer structure of the vacancy titanates instead of the sheared 3-block structure of, for example, $Na_2Ti_3O_7$, or the sheared 4-block structure of, for example, $K_2Ti_4O_9$, may reduce or eliminate shearing of the layers as a possible mechanism for thermal or hydrothermal decomposition of the calcined intercalated material.

The layered metal oxide starting material may be initially treated with a "propping" agent comprising a source of organic cation, such as organoammonium cation, in order to effect an exchange of the interspathic cations resulting in the layers of the starting material being propped apart. Suitable organoammonium cations include such as n-dodecylammonium, n-octylammonium, n-heptylammonium, n-hexylammonium, n-butylammonium and n-propylammonium. During this propping or swelling step it is important to maintain a low hydrogen ion concentration to prevent decomposition of the vacancy titanate structure as well as to prevent preferential sorption of hydrogen ion over the propping agent. A pH range of 6 to 10, preferably 7 to 8.5 is generally employed during treatment with the propping agent.

The foregoing treatment results in the formation of a layered metal oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion.

Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin, and lead. Other suitable oxides include those of Group VA, e.g., V, Nb, and Ta; those of Group IIA, e.g., Mg; or those of Group IIIB e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds e.g., alkoxides, of the desired elements of the pillars may be utilized as the precursors. Suitable polymeric silica precursor materials include tetraalkylsilicates, e.g., tetrapropylorthosilicate, tetramethylorthosilicate, and, most preferably, tetraethylorthosilicate. Suitable polymeric silica precursor materials also include quaternary ammonium silicates, e.g., tetramethylammonium silicate (i.e., TMA silicate). Where the pillars also include polymeric alumina, a hydrolyzable aluminum compound can be contacted with the organic "propped" species before, after, or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

Particular procedures for intercalating layered materials with metal oxide pillars are described in U.S. Pat. Nos. 4,831,005, 4,831,006: and 4,929,587. The entire disclosures of these patents are expressly incorporated herein by reference. U.S. Pat. No. 4,831,005 describes plural treatments with the pillar precursor. U.S. Pat. No. 4,929,587 describes the use of an inert atmosphere, such a nitrogen, to minimize the formation of extralaminar polymeric oxide during the contact with the pillar precursor. U.S. Pat. No. 4,831,006 describes the use of elevated temperatures during the formation of the pillar precursor.

It is preferred that the organic cation deposited between the layers be capable of being removed from the pillared material without substantial disturbance or removal of the interspathic aluminum. For example, organic cations such as n-octylammonium may be removed by exposure to elevated temperatures, e.g., calcination, in nitrogen or air, or by chemical oxidation.

These pillared layered products, especially when calcined, exhibit high surface area, e.g., greater than 200, 300, 400 or even 600 m²/g, and thermal and hydrothermal stability making them highly useful as catalysts or catalytic supports, for hydrocarbon conversion processes.

After calcination to remove the organic propping agent, the final pillared product may contain residual exchangeable cation Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

The pillared layered material catalyst support described herein is used to support a nickel catalyst component. Such component can be exchanged into the composition, impregnated therein or intimately physically admixed therewith. Such component can be impregnated in, or on, the layered material such as, for example, by treating the layered material with a solution containing a nickel metal-containing ion. Thus, a suitable nickel compound for this purpose includes nickel nitrate.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed by the thermal treatment, atmospheric pressure is preferred simply for reasons of convenience.

Prior to its use in organic conversion processes described herein, the catalyst should usually be dehydrated, at least partially. This dehydration can be done by heating the crystals to a temperature in the range of from about 200° C. to about 595° C. in an atmosphere such as air, nitrogen, etc., and at atmospheric, subatmospheric or superatmospheric pressures for between about 30 minutes and to about 48 hours. Dehydration can also be performed at room temperature merely by placing the layered material in a vacuum, but a longer time is required to obtain a sufficient amount of dehydration.

The catalyst can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded.

It may be desired to incorporate the catalyst with another material which is resistant to the temperatures and other conditions employed in the catalytic processes described herein. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the present catalyst, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate o reaction. These materials may be incorporated into naturally occurring clays, e.g., bentonite and kaolin, to improve the crus strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the ra state as originally mined or initially subjected to calcination, acid treatment or chemical modification. Binders useful for compositing with the catalyst- also include inorganic oxides, notably alumina.

In addition to the foregoing materials, the catalyst can be composited with a porous matrix material such as silica-alumina, silica-magnesia, silica-zirconia, silica-thoria, silica-beryllia, silica-titania as well as ternary compositions such as silica-alumina-thoria, silica alumina-zirconia, silica-alumina-magnesia and silica-magnesia-zirconia.

The relative proportions of finely divided layered catalyst and inorganic oxide matrix vary widely, with the catalyst content ranging from about 1 to about 90 percent by weight and more usually, particularly when the composite is prepared in the form of beads, in the range of about 2 to about 80 weight of the composite.

In the Examples which follow, whenever sorption data are set forth for comparison of sorptive capacities for water, cyclohexane and/or n-hexane, they were equilibrium adsorption values determined as follows:

A weighted sample of the calcined adsorbent was contacted with the desired pure adsorbate vapor in an adsorption chamber, evacuated to less than 1 mm and contacted with 21 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours As adsorbate was adsorbed by the layered material, the decrease in pressure caused the manostat to open a valve which admitted more adsorbate vapor to the chamber to restore the above control pressures. Sorption was complete- when the pressure change was not sufficient to activate the manostat. The increase in weight was calculated as the adsorption capacity of the sample in g/100 of calcined adsorbant.

EXAMPLE 1

Catalyst Preparation

A silica pillared vacancy titanate material was prepared as follows: 700 g (2.15 mole) $CsCO_3$ and 895.08 g (11.20 mole) of $TiO_2$ were ground together to homogeneity and fired at 650° C. for 10 hours. The sample was ball-milled for 4 hours at 30% solids, filtered and air dried. The ball-milled sample was exchanged with ammonium nitrate by stirring in a 1M solution (4000 cc $NH_4NO_3$/1500 g solid) at reflux for 6 hours. After 6 hours, the supernatant was decanted, and the exchange was repeated twice. Cs content was reduced to 1.6 wt.%.

Swelling of the solid was effected by treating the ammonium-exchanged solid in neat octylamine (3500 ml octylamine/1206 g solid) at reflux utilizing a Dean-Start trap i the condensation column. After 4 days, half the sample was removed. An additional 2000 ml octylamine was added to the flask, and reflux continued for an additional 2 days. The solid was then cooled, filtered, washed with 1000 ml ethanol, and air dried. The remaining solid was treated similarly, then blended. The solid was then treated with tetraethylorthosilicate (5 g TEOS/g solid) at 80° C. for 20 hours. An $N_2$ flow over the reactio prevented adventitious hydrolysis of TEOS by atmospheric moisture. The sample was filtered and dried in air. This sampl was then dispersed in water and stirred for 4 hours at room temperature, followed by filtration and drying in air. The TEOS/H₂O treatment was repeated twice.

The porous product was obtained by calcining in flowing air The sample obtained had the following properties:

| | | |
|---|---|---|
| SiO₂ | 67.8 | wt. % |
| Ti | 15.0 | wt. % |
| Cs | 0.55 | wt. % |
| C | <0.1 | wt. % |
| N | <0.03 | wt. % |
| Ash | 84.13 | wt. % |
| Surface area | 390 | m²/g |
| Adsorption properties (g/100 g) | | |
| H₂O | 14.5 | |
| c-C₆ | 9.7 | |
| n-C₆ | 7.3 | |

This silica pillared vacancy titanate material was used as catalyst support along 2 other supports made of silica gel (Davisil grade, 635, 60–100 mesh, surface area 480 m²/g, pore volume 0.75 cc/g, available from Aldrich Chemical Co.) and alumina (160 m²/g, available from Alpha Chemical Co.). These 3 supports were impregnated with a nickel nitrate solution. More particularly, a nickel nitrate stock solution was prepared by dissolving 72.75 g Ni(NO₃)₂6H₂O in 500 cc distilled water. Each of the 3, above-mentioned solid supports, 50 g each, in powder form, was mixed with 100 cc of the stock nickel solution and stirred for half an hour at room temperature. The liquid was then filtered. The dry catalysts were first calcined at 200° C. under nitrogen for 16 hours and then further calcined with air a 500° C. for 16 hours.

EXAMPLE 2

Ethylene Oligomerization

Each of the catalysts prepared in accordance with Example 1 was used to oligomerize ethylene by the same reaction.

The oligomerization reaction was carried out in a 1 liter autoclave. The autoclave, containing 15 g catalyst, was purged with nitrogen for 16 hours at 150° C. Then 150 cc dodecane solvent was added. When the reaction temperature was stabilized at 150° C., 350 g of ethylene was charged into the reactor in 4.0 hours. Reactor pressure reached 500 psi and dropped quickly to 160 psi in 3 hours. The product was analyzed by gc. The result are summarized in Table 1 Table 1 also includes literature information about ethylene oligomerization over other supported catalysts as reported in U.S. Pat. Nos. 4,942,021 (Ni/ZSM-5) and 3,527,839 (Ni/SiO₂-Al₂O₃). The nickel on alumina and nickel on silica gel catalysts prepared in Example 1 showed very low activity for ethylene conversion. The product contained mostly butenes.

TABLE 1

Reaction Conditions and Product Compositions of Ethylene Oligomerization by Different Supported Ni Catalysts

| Catalyst type Source | Ni/VTM this work | Ni/ZSM-5 U.S. Pat. No. 4,942,021 | Ni/ SiO₂—Al₂O₃ U.S. Pat. No. 3,527,839 |
|---|---|---|---|
| Reaction Conditions | | | |
| Temperature, °C. | 150 | 121 | 150 |
| Pressures, psig | 160–400 | 400 | 400 |
| Catalyst productivity, g of oligomers/g of catalyst/hour | 3.2 | 0.5 | 3.2 |
| Average product molecular weight | 112 | 78 | 60 |
| Product composition, wt. % | | | |
| C₄ | 13.2 | 40.8 | 85.4 |
| C₆ | 20.7 | | 9.6 |
| C₈ | 16.7 | 40.9 | 2.3 |
| C₁₀ | 14.9 | | 1.1 |
| C₁₂ | 9.1 | | 0.6 |
| C₁₄ | 6.0 | 13.5 | 0.5 |
| C₁₆ | 1.8 | | 0.3 |
| C₁₆+ | 17.7 | 1.7 | 0.2 |
| Others | 0 | 3.4 | 0 |
| Comments | linear or iso-olefins | iso-olefins | linear,α-olefins |

What is claimed is:

1. A process for oligomerizing ethylene, said process comprising contacting ethylene with a catalyst under sufficient oligomerization conditions, wherein said catalyst comprises nickel supported on a pillared layer vacancy titanate material wherein each layer of said layered vacancy titanate material has the formula $$[\square_y Ti_{2-y} O_4]^{q-}$$

where $\square$ represents a vacancy site, $0 < y < 2$ and $q = 4y$.

2. A process according to claim 1, wherein said pillared layered vacancy titanate material is pillared with silica.

3. A process according to claim 1, wherein nickel is placed on said catalyst by an ion exchange process.

4. A process according to claim 1, wherein nickel is placed on said catalyst by an impregnation process.

5. A process according to claim 1, wherein said catalyst is prepared by a method comprising the steps of:
   (a) contacting a pillared layered vacancy titantate material with a solution of a nickel compound under conditions sufficient to sorb at least a portion of said nickel compound into porous regions of the pillared layered vacancy titantate material;
   (b) drying the contacted material of step (a) under conditions sufficient to leave a residue of said nickel compound in porous regions of the pillared layered vacancy titanate material; and
   (c) calcining the dried material of step (b) under conditions sufficient to convert said residue into nickel oxide.

6. A process according to claim 5, wherein said solution of a nickel compound is an aqueous solution of nickel nitrate.

* * * * *